United States Patent [19]

Roberts

[11] 4,152,928
[45] May 8, 1979

[54] SYSTEM FOR DETECTING FAT PARTICLES IN BLOOD

[75] Inventor: Richard A. Roberts, Boulder, Colo.

[73] Assignee: University Patents, Inc., Norwalk, Conn.

[21] Appl. No.: 792,893

[22] Filed: May 2, 1977

[51] Int. Cl.² .................... G01N 15/00; G01N 29/02; G01N 33/16

[52] U.S. Cl. ................. 73/61 R; 73/194 A; 128/663

[58] Field of Search ............ 73/61.1 R, 61 R, 194 A; 128/2.05 F

[56] References Cited

U.S. PATENT DOCUMENTS

| | | | |
|---|---|---|---|
| 3,550,070 | 12/1970 | McLeod, Jr. | 73/194 A X |
| 3,554,030 | 1/1971 | Peronneau | 73/194 A |
| 3,640,271 | 2/1972 | Horton | 73/194 A X |
| 3,675,192 | 7/1972 | Fahrbach | 73/194 A X |
| 3,732,532 | 5/1973 | Flaherty et al. | 73/194 A X |
| 3,896,788 | 7/1975 | Sato | 73/194 A X |
| 3,921,622 | 11/1975 | Cole | 73/61 R X |
| 3,922,911 | 12/1975 | Groves et al. | 73/194 A |
| 3,974,683 | 8/1976 | Martin | 73/61 R X |

OTHER PUBLICATIONS

McCarty and Woodcock, *The Ultrasonic Doppler Shift Flowmeter—A New Development,* in Biomedical Eng., pp. 336-340, Aug. 1974.

Jacobson, J. O. et al., *Ultrasonic Detection of Bloodstream Emboli.*, Ocean 1973 IEEE Conference, pp. 141-147, Sep. 1973.

Nishi, R. Y., *Ultrasonic Detection of Bubbles with Doppler Flow Transducers,* Ultrasonics, pp. 173-179, July 1972.

*Primary Examiner*—Richard C. Queisser
*Assistant Examiner*—Joseph W. Roskos
*Attorney, Agent, or Firm*—Martin Novack

[57] ABSTRACT

A system utilizing a bank of frequency staggered bandpass filters spanning the range in which fat emboli are known to occur is provided for the early detection of fat emboli in blood.

13 Claims, 1 Drawing Figure

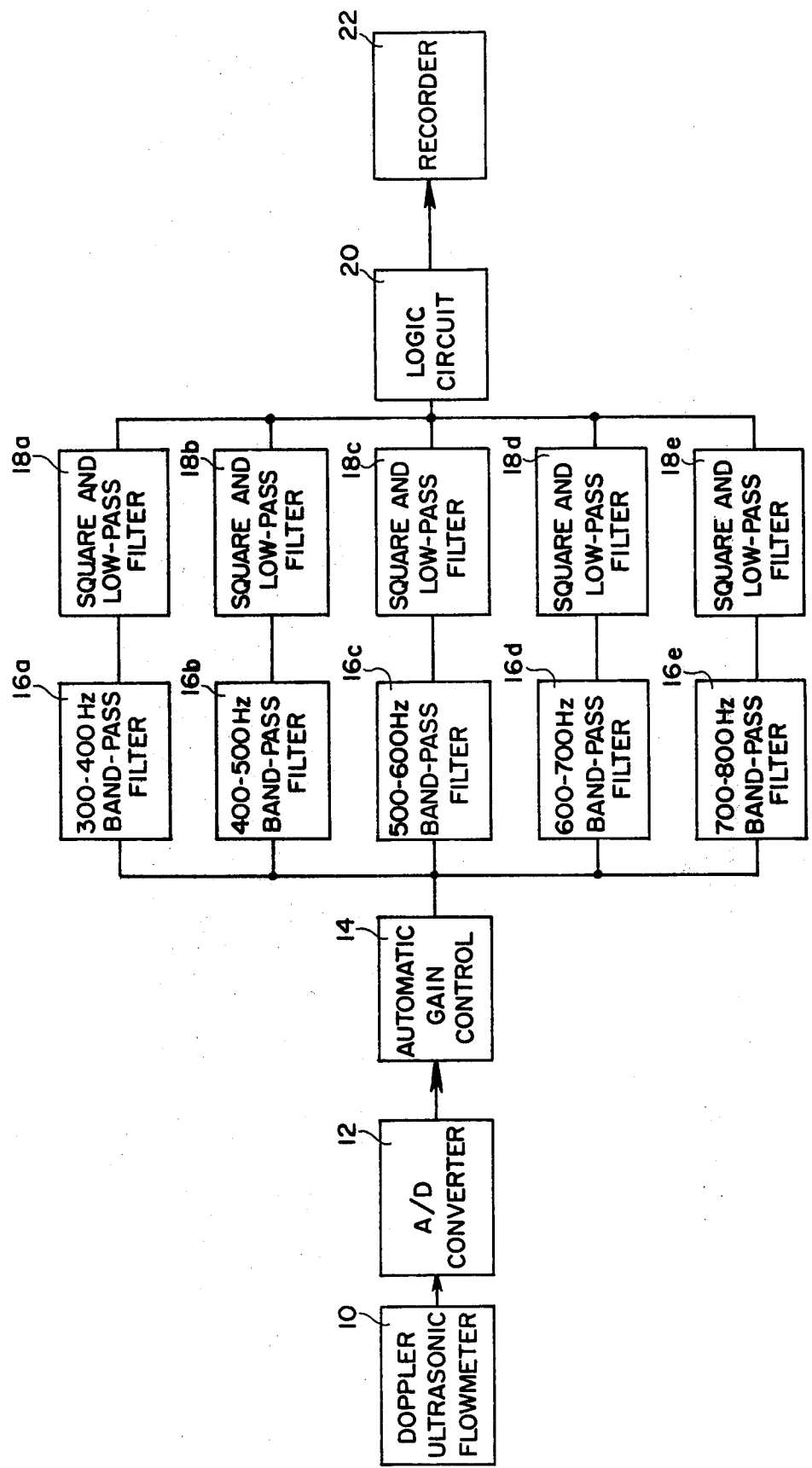

SYSTEM FOR DETECTING FAT PARTICLES IN BLOOD

BACKGROUND OF THE INVENTION

The detection of intravascular fat emboli (fat emboli are tiny globules of fat frequently found in the blood after a long bone fracture) following long bone fracture is necessary to insure timely therapy. The restriction or blockage of a blood vessel by a fat embolus can lead to the death of those body cells dependent on that circulation supply. The presence of fat emboli in the bloodstream, often referred to as the Fat Embolism Syndrome (FES), can cause pulmonary edema, apoplexy, or death.

The well-known continuous wave doppler ultrasonic flowmeter can be used to measure blood flow velocity and to detect gaseous emboli in the bloodstram. In recent experiments Kelly, Dodi and Eiseman have successfully detected the presence of fat emboli in the venous flow in the vicinity of a long bone fracture for a short period of time after the occurrence of the fracture. The detection is based on audio output of the flowmeter. A trained listener can hear certain "embolic sounds" in the audio output of the flowmeter. This work is described in Surgical Forum, Vol. XXIII (1972), pages 459-460.

The primary object of this invention is to provide a simple, reliable, robust and inexpensive technique to enhance and quantify the detection of FES in earliest stages.

SUMMARY OF THE INVENTION

The present invention is directed to the non-invasive detection of fat particles in blood vessels. In a preferred embodiment, ultrasound energy at 9.2 MHz is directed into the blood vessels suspected of containing suspended fat particles. The doppler signal is then obtained from the reflected or backscattered ultrasound signal. This doppler signal is converted to a digital representation. This digital signal is passed through a bank of parallel digital filters. The outputs of these 5 filters are then compared sample by sample. A decision circuit, which always outputs the largest of the 5 filter outputs, follows the bank of filters. When fat particles are present, the output of this instrument is large. When no fat particles are present, the output is small.

BRIEF DESCRIPTION OF THE DRAWING

FIG. 1 is a schematic block diagram representation of an apparatus in accordance with an embodiment of the invention.

DESCRIPTION OF THE PREFERRED EMBODIMENT

By visual inspection of the output of a doppler ultrasonic flowmeter, such as the flowmeter 10, containing "embolic sounds," suspected fat emboli sounds or "signatures" were identified. These suspected signatures were then analyzed as to time duration, frequency of occurrence and frequency content (using their power spectrum as a measure). The frequency of occurrence of the signatures averaged 5 per second. Perhaps the most important characterization of these signatures is their power spectrum. The power spectrum of the signatures was a single peak between 300 and 800 Hz. The width of this single peak at the half power points varied from 50 to 120 Hz. The majority of the peaks were in the 400-600 Hz range. Thus, I have determined that the fat emboli are randomly occurring events, averaging 5 per second, their time duration varies from 10 to 50 milliseconds, and they contain frequencies in a band from 50 to 120 Hz wide in the range from 300 to 800 Hz. The flowmeter 10 used is a Parks, Model 803-DUF.

By examining doppler returns with and without fat emboli present, a characterization of the doppler return from fat emboli is possible. This signature changes as does the noise background. The detection problem is thus one of detecting a time varying, aperiodic occurring, signal in a time varying noise background.

Cross-correlation of matched filtering as shown in FIG. 1, is the most powerful method of detecting known signals in stationary noise, Using a bank of frequency staggered band-pass filters 16a-16e, spanning the frequency range in which fat emboli are known to occur, a good detector is provided. Each filter 16 in the illustrated embodiment is a four-pole, type 1, chebyshev filter with 1dB pass-band ripple.

In operation, the flowmeter 10 is used to monitor blood flow transcutaneously, such as at the femoral vein of a patient having a long-bone fracture. The audio output from flowmeter 10 is digitized by A to D converter 12 and this output therefrom fed to automatic gain control unit 14. The digitized signals are then fed to the parallel, frequency staggered filters 16a-16e. The outputs of these filters 16a-16e are fed to the adjacent low-pass filters 18a-18e. Each filter is preferably 100 Hz in bandwidth, and five filters are used to cover the range from 300 to 800 Hz in view of the above-mentioned determination regarding the nature of fat emboli in the blood.

Logic circuit 20, which may comprise a comparator and a plurality of gates, compares the five outputs from the filters 18a-18e sample by sample. This circuit 20 passes the largest output of each sample, which output is recorded by recorder 22. This recorder may be either an audio or visual recorder. When fat particles are present, the output signal to the recorder is large and vice versa.

I claim:

1. A system for producing signals indicative of the presence of fat particles in blood comprising, in combination:
    a doppler ultrasonic flowmeter for generating an electrical signal representative of blood flow characteristics;
    means responsive to said signal for detecting a peak of the power spectrum of said signal in relatively narrow frequency bands, having widths in the range between 50 and 120 Hz., over a relatively wide frequency range which includes a plurality of said narrow frequency bands; and
    means for recording said detected peak.

2. The system as defined by claim 1 wherein said relatively wide frequency range is the range of about 300 to 800 Hz.

3. A system for producing signals indicative of the presence of fat particles in blood comprising, in combination:
    a doppler ultrasonic flowmeter for generating an electrical signal representative of blood flow characteristics;
    means responsive to said signal for detecting a peak of the power spectrum of said signal in relatively narrow frequency bands over a relatively wide frequency range which includes a plurality of said narrow frequency bands, said relatively wide frequency range being the range of about 300 to 800 Hz.; and means for recording said detected peak.

4. A system for producing signals indicative of the presence of fat particles in blood comprising, in combination:
- a doppler ultrasonic flowmeter for generating an electrical signal representative of blood flow characteristics;
- means responsive to said signal for detecting a peak of the power spectrum of said signal in relatively narrow frequency bands over a relatively wide frequency range which includes a plurality of said narrow frequency bands; and
- means for recording said detected peak.

5. The system as defined by claim 4 wherein the filter bandpasses are in the range of 50 to 120 Hz wide.

6. The system as defined by claim 4 wherein the total range covered by the filter bandpasses is about 300 to 800 Hz.

7. The system as defined by claim 5 wherein the total range covered by the filter bandpasses is about 300 to 800 Hz.

8. The system as defined by claim 4 wherein said bank of parallel bandpass filters comprises five filters, each having a contiguous bandpass about 100 Hz wide in the total range of about 300 to 800 Hz.

9. The system as defined by claim 4 further comprising means for converting said signal to digital form, and wherein said filters are digital filters.

10. The system as defined by claim 5 further comprising means for converting said signal to digital form, and wherein said filters are digital filters.

11. The system as defined by claim 6 further comprising means for converting said signal to digital form, and wherein said filters are digital filters.

12. The system as defined by claim 7 further comprising means for converting said signal to digital form, and wherein said filters are digital filters.

13. The system as defined by claim 8 further comprising means for converting said signal to digital form, and wherein said filters are digital filters.

* * * * *